United States Patent [19]

Fischer

[11] Patent Number: Plant 5,726

[45] Date of Patent: Apr. 22, 1986

[54] AFRICAN VIOLET PLANT NAMED CORSAIRE

[75] Inventor: Arnold Fischer, Hanover, Fed. Rep. of Germany

[73] Assignee: Pan American Plant Co., Parrish, Fla.

[21] Appl. No.: 632,102

[22] Filed: Jul. 18, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct African violet named Corsaire, particularly characterized by its large pale pink flowers with darker red-purple center, the flowers being borne in a cluster above dark green foliage, profuse and intermittent year round flowering.

1 Drawing Figure

The present invention comprises a new and distinct cultivar of African violet plant, botanically known as *Saintpaulia ionantha,* and hereinafter referred to by the cultivar name Corsaire.

The new cultivar was referred to during the breeding and selection process by the designation V7-E10-P, and is a product of a planned breeding program. The basic objective of the breeding program was to create a new African violet cultivar having profuse, large, light pink, slightly ruffled blooms above dark, green foliage. The new cultivar was originated from a cross made in a controlled breeding program in Hannover, Germany. The male and female parents are unknown at this time.

Corsaire was discovered and selected by me as a flowering plant within the progeny of the stated cross in a controlled environment in Fallbrook, Calif. Asexual reproduction of the new cultivar by leaf cuttings, as performed by me at West Chicago, Ill. and Parrish, Fla. has demonstrated that the combination of characteristics as herein disclosed for the new cultivar are firmly fixed and retained through successive generations of asexual reproduction.

Corsaire has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Corsaire which in combination distinguish this African violet as a new and distinct cultivar:

(1) Very large pale pink flowers, with darker red-purple color in centers.

(2) Flowers are borne in a cluster above dark green foliage.

(3) Profuse flowering.

The new cultivar is most similar to Marta, disclosed in U.S. Plant Pat. No. 3,610. Corsaire is principally distinguished from Marta by its pale pink flowers borne on strong stems above the dark green foliage.

The accompanying color photographic drawing shows a typical specimen plant of the new cultivar. The colors appearing in the photograph are as true as possible with color illustrations of this type.

In the following description, color references are made to The Royal Horticultural Society Color Chart (R.H.S.), except where general colors of ordinary significance are referred to. Color values were taken under 5000 foot candles of natural light at approximately 12:00 P.M. in Parrish, Fla.

BOTANICAL CLASSIFICATION: *Saintpaulia ionantha,* Ramat. cv. Corsaire.

Parentage:

*Male parent.*—Unknown.

*Female parent.*—Unknown.

Propagation: The new cultivar holds its distinguishing characteristics through successive propagations by leaf cuttings.

Plant: From 6 cm. to 9 cm. tall when grown in pots, and approximately 24 cm. in diameter when fully grown. The growth rate is vigorous, and the general shape of the full grown plant is round.

Leaves:

*Quantity.*—Abundant.

*Shape.*—Cordate with crenate margins.

*Diameter.*—5–8 cm.

*Texture.*—Pubescent, glossy.

*Ribs and veins.*—Pinnate.

*Color (upperside).*—147A.

*Color (underside).*—59A.

*Petioles.*—2–8 cm. in length.

Flowers:

*Buds.*—Size: Up to 1 cm. in diameter. Shape: Round. Rate of opening: Normal. Color: Ranging from 70B to 70D.

*Sepals.*—Shape: Lanceolate. Color: 183B with a tint of 147D.

*Phyllaries.*—2, Lanceolate. Color (upperside): 147A. Color (underside): 59A.

*Calyx.*—Shape: Funnel. Size: About 12 mm. in diameter.

*Peduncle.*—Length: 3–7 cm. Character: Rigid, erect. Color: 183A with a tint of 147D.

*Individual flowers.*—Number of petals: 5. Size: 25–47 mm. in diameter and 10–15 mm. deep. Shape: Cup shaped when bloom first opens, becoming flat with maturity. Color: Upperside: 73D with hints of 72B in center. Underside: 65C.

*Borne.*—Cymose clusters form on peduncles 3–7 cm. long.

*Flowering habit.*—Flowers profusely and intermittently year round with blooms lasting 2–3 weeks after which petals dry up but do not drop. A $2\frac{1}{2}''$ plantlet grown in a 10 cm. pot finishes in 9–12 weeks.

*Reproductive organs.*—Stamens: 2, borne singly on one side of the ovary. Anthers basifixed. Anthers: 2 mm.×2 mm.×yellow. Filaments: 2–3 mm., yellow. Pollen color: Yellow.

*Pistils.*—Number: 1, 4–7 mm. long. Styles: 1. Stigma: sticky, white. Ovaries: superior.

*Roots.*—Fibrous and fine.

*Disease resistance.*—No African violet diseases observed to date.

General observations: Corsaire is principally characterized by its large flowers which are borne in a tight bouquet above the dark green foliage. The flower color is a pale pink with a darker red-purple center, and occasional darkening around the ruffled petal edges.

I claim:

1. A new and distinct cultivar of African violet named Corsaire, as illustrated and described, and particularly characterized by its large, pale pink flowers with darker red-purple center, the flowers being borne in a cluster above dark green foliage, profuse and intermittent year round flowering.

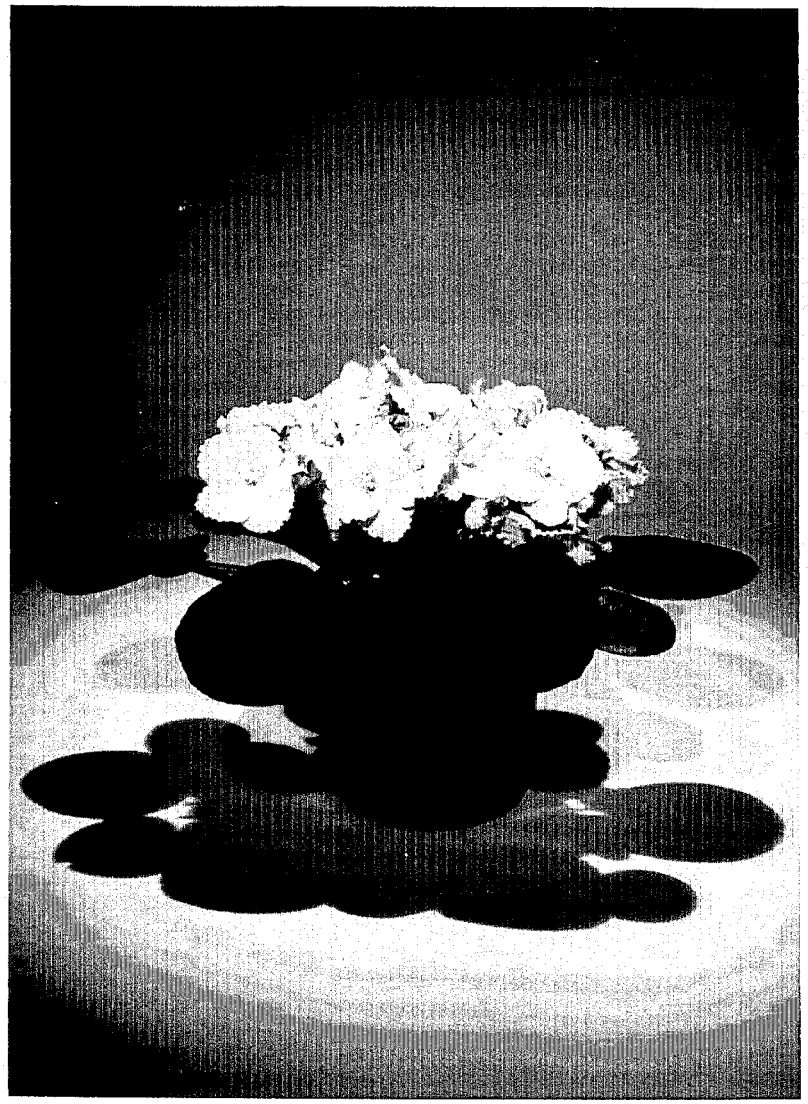

* * * * *